United States Patent [19]

Davies

[11] Patent Number: 5,601,693
[45] Date of Patent: Feb. 11, 1997

[54] GAS SENSOR

[75] Inventor: David F. Davies, Locks Heath, United Kingdom

[73] Assignee: City Technology Limited, Portsmouth, United Kingdom

[21] Appl. No.: 375,856

[22] Filed: Jan. 20, 1995

[30] Foreign Application Priority Data

Jan. 28, 1994 [GB] United Kingdom .................. 9401634

[51] Int. Cl.$^6$ .......................... G01N 27/12; G01N 27/26
[52] U.S. Cl. .......................... 204/400; 204/424; 204/431; 422/98
[58] Field of Search ............................ 204/400, 421–429, 204/431; 422/98

[56] References Cited

U.S. PATENT DOCUMENTS

| | | | |
|---|---|---|---|
| 3,607,710 | 9/1971 | Farren et al. | 204/419 |
| 3,707,455 | 12/1972 | Derr et al. | 204/415 |
| 4,121,989 | 10/1978 | Shum et al. | 204/428 |
| 4,272,350 | 6/1981 | Croset et al. | 204/426 |
| 4,502,939 | 3/1985 | Holfelder et al. | 204/426 |
| 4,507,643 | 3/1985 | Sunano et al. | 422/98 |
| 4,963,245 | 10/1990 | Weetall | 204/412 |
| 5,047,214 | 9/1991 | Fukui et al. | 422/98 |
| 5,057,436 | 10/1991 | Ball | 422/98 |
| 5,183,549 | 2/1993 | Joseph et al. | 204/153.17 |
| 5,223,783 | 6/1993 | Willis | 422/98 |

FOREIGN PATENT DOCUMENTS

| | | |
|---|---|---|
| 0032844 | 7/1981 | European Pat. Off. . |
| 0346127 | 12/1989 | European Pat. Off. . |
| 3046560 | 7/1982 | Germany . |
| 3743398 | 7/1989 | Germany . |
| 4218883 | 12/1993 | Germany . |
| 2204184 | 11/1988 | United Kingdom . |

*Primary Examiner*—T. Tung
*Attorney, Agent, or Firm*—Lee, Mann, Smith, McWilliam, Sweeney & Ohlson

[57] ABSTRACT

A device for sensing a gas comprises a pair of gas sensitive elements (25,26) surface mounted via conductors to a track carrying substrate (23).

17 Claims, 4 Drawing Sheets

GAS SENSOR

FIELD OF THE INVENTION

This invention relates to a device for sensing a combustible gas or vapour in air.

DESCRIPTION OF THE PRIOR ART

Conventional catalytic oxidation devices for sensing combustible gases or vapours incorporate an electrically heated platinum coil embedded within a detector bead. At the appropriate temperature the gas or vapour to be measured is catalytically oxidised on the detector bead. Heat is evolved during this process thereby increasing the temperature and, consequently, the electrical resistance of the platinum coil contained within the bead. This change in resistance is a measure of the amount of combustible gas or vapour present in the atmosphere under test. In a complete device a second, compensator bead is also employed to compensate for changes in ambient conditions, such as temperature, which could provide erroneous results. The matched pair of detecting and compensating beads are conveniently employed within a Wheatstone bridge measurement circuit providing a signal which is proportional to the concentration of combustible gas or vapour in the atmosphere under test.

For the above arrangement to function satisfactorily as a gas sensor it is clear that certain criteria must be met. Since both detector and compensator beads operate at temperatures of about 500° C., it is important that the beads are supported in a manner which prevents an unacceptable level of heat loss from the bead. In conventional devices this is normally achieved by supporting the beads on electrically conducting arms extending vertically above a base, the other ends of the arms extending through the base to provide electrical leads for connection into the measurement circuitry. In this manner, the beads are maintained in a position which minimises heat loss from the beads but which still allows electrical heating and access of the test gas to the beads.

There are disadvantages to this conventional arrangement, the greatest of these being that the device has a minimum length of about 8 mm resulting from the need to support the beads an adequate distance above the base. In addition, where the devices are produced for incorporation onto printed circuit boards (pcb), a further increase in height occurs due to the board thickness. Finally, the overall height of the complete gas sensor is further increased by regulatory requirements designed to ensure safe operation of the sensor in potentially explosive atmospheres. These include a minimum depth of potting compound, sinter thickness required to prevent flame propagation, and means for protecting the sinter from impacts.

SUMMARY OF THE INVENTION

In accordance with the present invention a device for sensing a gas comprises at least one gas sensitive element surface mounted via conductors to tracks on a track carrying substrate.

The arrangement of the present invention allows a device to be fabricated in which the at least one gas sensitive element is mounted so that the overall height of the device is considerably less than a conventional device. Despite this reduction in height, it has been found surprisingly that any increase in heat loss can be compensated by a relatively small increase (e.g. 10%) in power supplied to the device.

Preferably the device further comprises a sinter layer mounted on one side of the substrate; a layer of potting compound provided on the other side of the substrate; means for protecting the sinter layer; and a separating member to isolate the at least one gas sensitive element from the potting compound.

The thicknesses of the sinter layer, the sinter protection and the layer of potting compound depend upon national regulatory requirements. In the UK the sinter layer is typically 3 mm thick with a protective edge of approximately 2 mm while the potting compound typically has a minimum thickness of 3 mm.

Preferably the separating member is formed from one of ceramic, plastic or printed circuit board, although other materials could be used. An additional layer of glass or ceramic wool may be provided to protect the elements.

Preferably the device further comprises a housing in which the track carrying substrate is mounted. Typically the housing is made of metal such as stainless steel, brass, aluminium etc., although the sinter layer, when provided, could be extended to form the housing.

Preferably the substrate comprises a printed circuit board, glass or ceramic.

Having surface mounted the at least one gas sensing element directly onto the substrate, a gas sensor may be produced offering facilities such as signal processing without the need for separate, additional electronics. For example, electronic circuitry could be screen printed onto the substrate, supporting the gas sensitive (pellistor) element(s), which could include items such as, the basic Wheatstone bridge in which the elements are connected, an amplified mA or mV-signal output, a temperature sensor, data collection and processing functions contained within a memory and/or microprocessor, etc.

Generally the at least one gas sensitive element is mounted over an aperture cut through the substrate so that the gas which is being sensed can reach the element. Preferably, the at least one gas sensitive element is positioned wholly within a respective aperture in the substrate. This increases the physical protection for the element and also minimises the risk of contact between the element and other parts of the device, for example protecting glass wool if provided.

Preferably, the device further comprises a second gas sensitive element wherein the second element is a compensating element and the first a detecting element.

The at least one gas sensing element may be manufactured in situ, but preferably the or each element is preformed before mounting to the track carrying substrate.

Typically, the at least one gas sensing element comprises a catalytic bead.

BRIEF DESCRIPTION OF THE DRAWINGS

An example of a gas sensor incorporating a device for sensing a gas in accordance with the present invention will now be described and compared with a conventional sensor with reference to the accompanying drawings in which.

DETAIL DESCRIPTION OF PRIOR ART AND EMBODIMENTS

Figure 1:
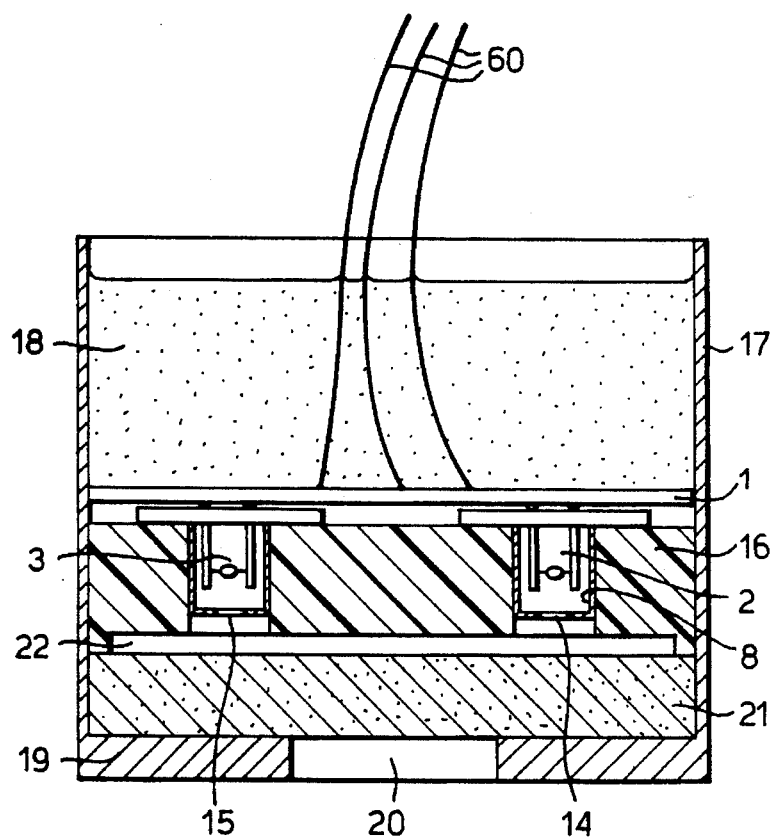
FIG. 1 shows a conventional gas sensor.
Figure 2:
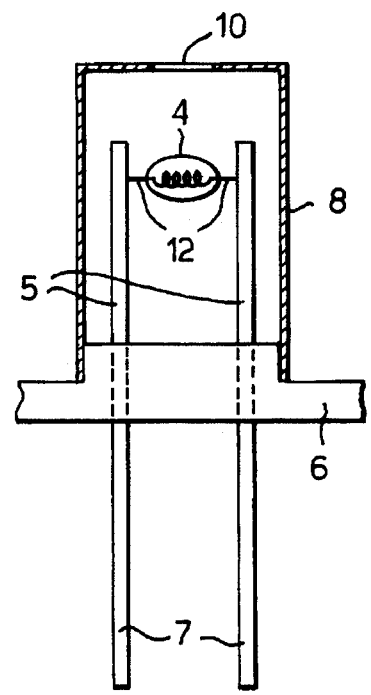
FIG. 2 shows the gas sensing device of FIG. 1 in more detail.

The gas sensor shown in FIG. 1 comprises a printed circuit board 1 to which is mounted a conventional gas sensing device 2 and a conventional compensating device 3. The construction of the devices 2,3 is shown in more detail in FIG. 2. As shown in FIG. 2, each device comprises a gas sensing element 4 suspended between a pair of electrically conducting arms 5 which extend through a base 6 to form extensions 7 which define electrical leads for connecting to the printed circuit board. A casing 8, made for example of stainless steel, is secured over the gas sensing element 4 and is spot welded to the base 6. Gas to be detected can enter into the casing 8 via an aperture 10.

Figure 3:
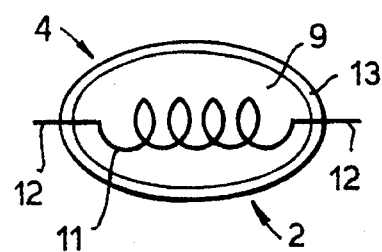
FIG. 3 shows a catalytic bead in detail.

Each of the devices 2,3 is constructed as shown in FIG. 3, the only difference lying in the form of the gas sensing element 4. As shown in FIG. 3, the gas sensing element 4 forming part of the device 2 includes a coil 11 made of platinum (although any other similarly unreactive metal could be used) terminating in a pair of leads 12 which are connected to the respective pair of arms 5. The coil 11 is coated with, for example, ceramic material 9 forming a bead. In the case of the device 2, the ceramic material is additionally coated with a layer 13 of a catalyst which may be chosen according to the gas which is to be detected. In an alternative arrangement (not shown), the ceramic material could be impregnated with the catalyst.

The ceramic bead 9 of the gas sensing element 4 of the device 3 is not provided with catalyst so that it can act as a compensator.

Each bead typically is in the form of a spheroid with a diameter of about 0.25–1.00 mm.

The devices 2,3 are positioned in respective apertures 14,15 of a block of PTFE 16. The block 16 rests against the printed circuit board 1 and is mounted in a housing 17 closed at one end by a layer of potting compound 18 which prevents flame propagation in that direction. Electrical leads 60 are connected to the extensions 7 (which are cut to size) via the printed circuit board 1 and to a monitoring circuit of the type shown in FIG. 7.

The housing 17 has an inturned flange 19 defining an aperture 20 and behind which is secured a layer of porous sinter 21 to act as a flame trap for the device which typically operates at around 500° C. and could ignite the gas being monitored. The potting compound 18 is secured within the casing 17 such that the printed circuit board 1, PTFE insert 16, and porous sinter 21 are urged together.

In use, gas passes into the sensor through the aperture 20 and the sinter 21 and then through the respective apertures 10 in the casings 8 of the two devices 2,3.

It will be noted that a small gap 22 is formed between the sinter 21 and the majority of the insert 16 to allow good distribution of the gas entering the sensor.

The sensor operates in a conventional manner such as is described in "Solid State Sensors". Edited by P. T. Moseley and B. C. Tofield, published by Adam Hilger 1987.

The main problem with this conventional sensor is that it takes up a relatively large volume of space defined primarily by the height of the elements 4 above the base 6 which reduces heat loss by convection, and the thickness of the base 6 and the printed circuit board 1.

Figure 4:
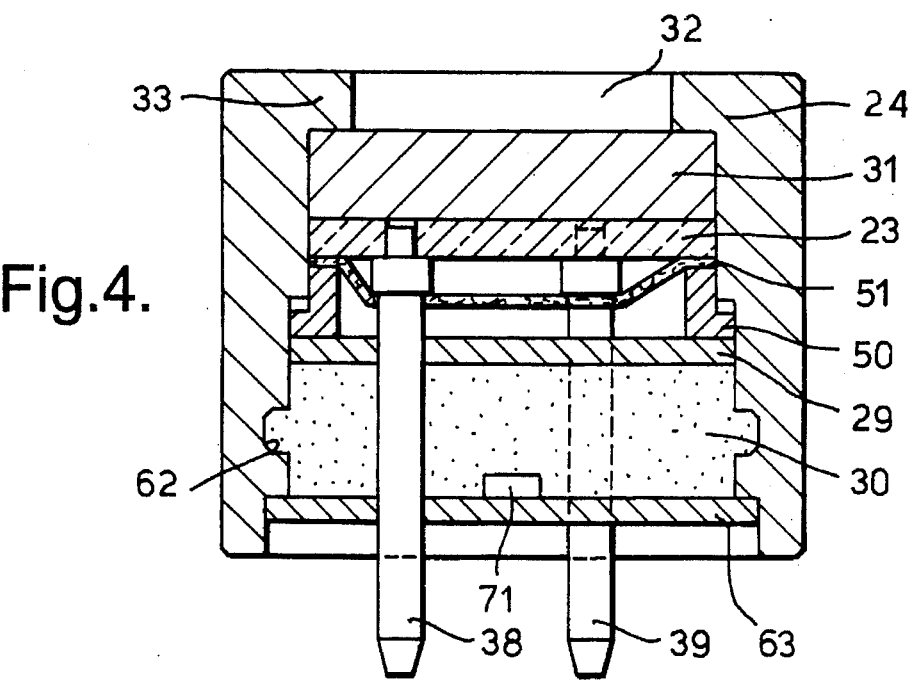
FIG. 4 is a section through a gas sensor according to the present invention.
Figure 5:
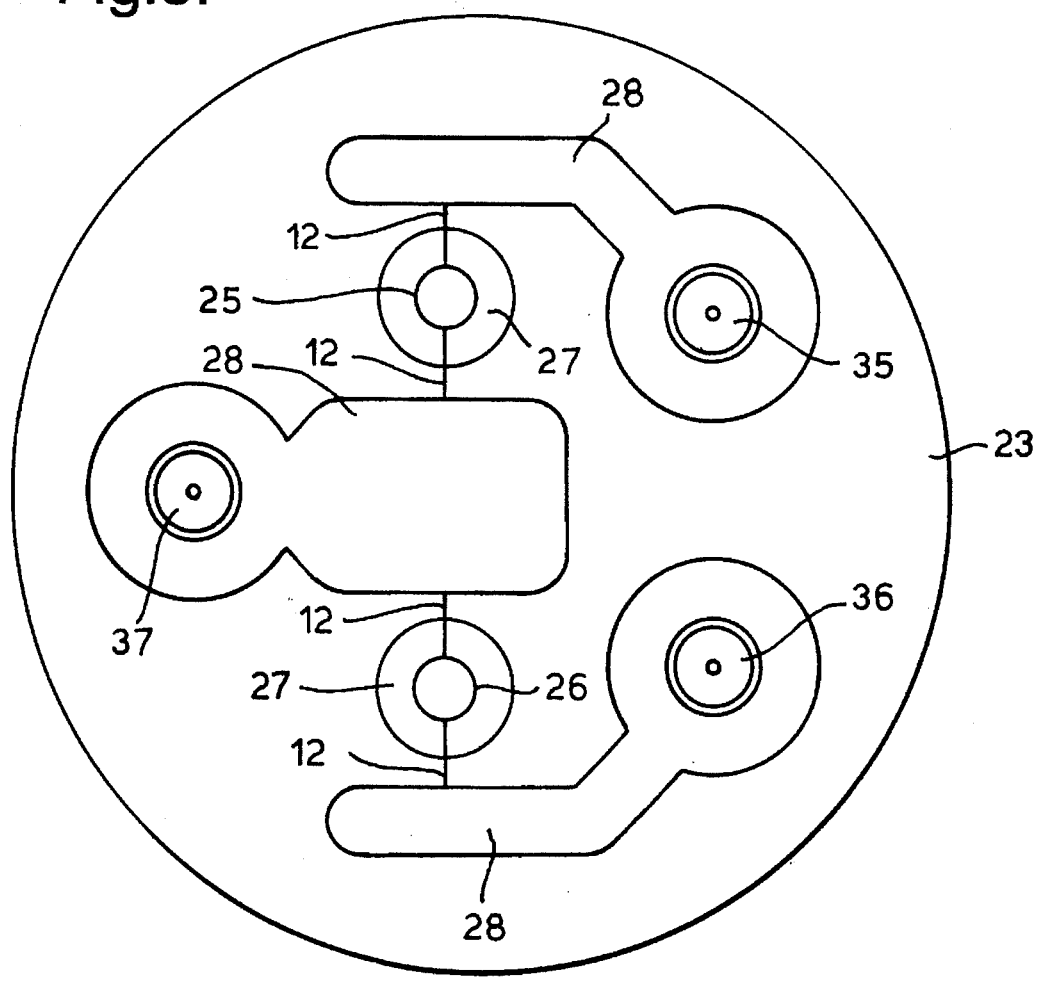
FIG. 5 is a plan view of the substrate of the device as shown in FIG. 4.

One example of a sensor incorporating devices according to the present invention is shown in FIGS. 4 and 5. A ceramic substrate 23 or other substrate, for example a printed circuit board, is mounted in a housing 24, typically made of stainless steel. The ceramic substrate 23 supports a pair of gas sensing elements, a compensator element 25 and a detector element 26. The gas sensing elements have a similar construction to those described above. The elements are mounted within openings 27 in the substrate 23. Leads 12 from the elements 25,26 are connected (surface mounted) to electrical tracks 28 on a surface of the substrate 23 as shown in FIG. 5 using conducting cement or by welding etc.

Figure 8:
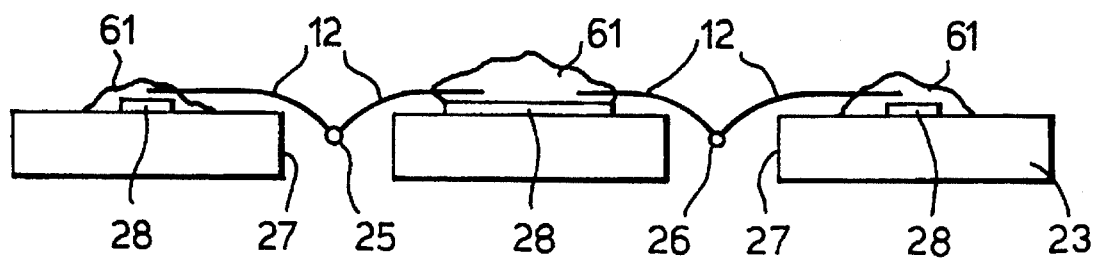
FIG. 8 is a cross-section through the substrate shown in FIG. 4 with connectors omitted; and, FIG. 9 is an underneath plan of the rear closing plate shown in FIG. 4.

The arrangement of the elements 25,26 can be seen most clearly in FIG. 8. The element 25 is suspended in the aperture 27 by its leads 12 which are electrically connected to respective tracks 28 by silver paste 61. Similarly, the element 26 is suspended in its aperture 27 by leads 12 electrically connected to tracks 28 with the silver paste 61. In a typical arrangement, the depth of each aperture 27 is about 1.27 mm and its diameter 2 mm. As can be seen in FIG. 8, the elements 25,26 are fully contained within the apertures 27 although in some cases they could partially protrude above the apertures or even be positioned fully above the apertures.

The substrate 23 is clamped against a sinter layer 31 in the housing 24 by means of a compression ring 50. The compression ring 50 also serves to retain a layer 51 of inert, insulating material such as glass or ceramic wool in position between the beads 25,26 and a separating layer 29. The layer 51 essentially removes the effect of changes in orientation on the sensor by substantially preventing convection currents and improves the shock resistance of the device. Similar material could also be provided in the apertures 27 on the sinter layer side. The separating member 29 is provided to separate and protect the elements 25,26 and the layer 51 from a layer of potting compound 30. The separating member 29 may be a printed circuit board, or a ceramic or plastic cover. A groove 62 is provided around the inner surface of the housing 24 so that the potting compound can be provided with a key.

Three connectors, two of which 38,39 are shown in FIG. 4, extend upwardly from the tracks 28 at 35–37. These connectors provide electrical connections to the measurement or monitoring circuitry which is to be described below.

Figure 9:
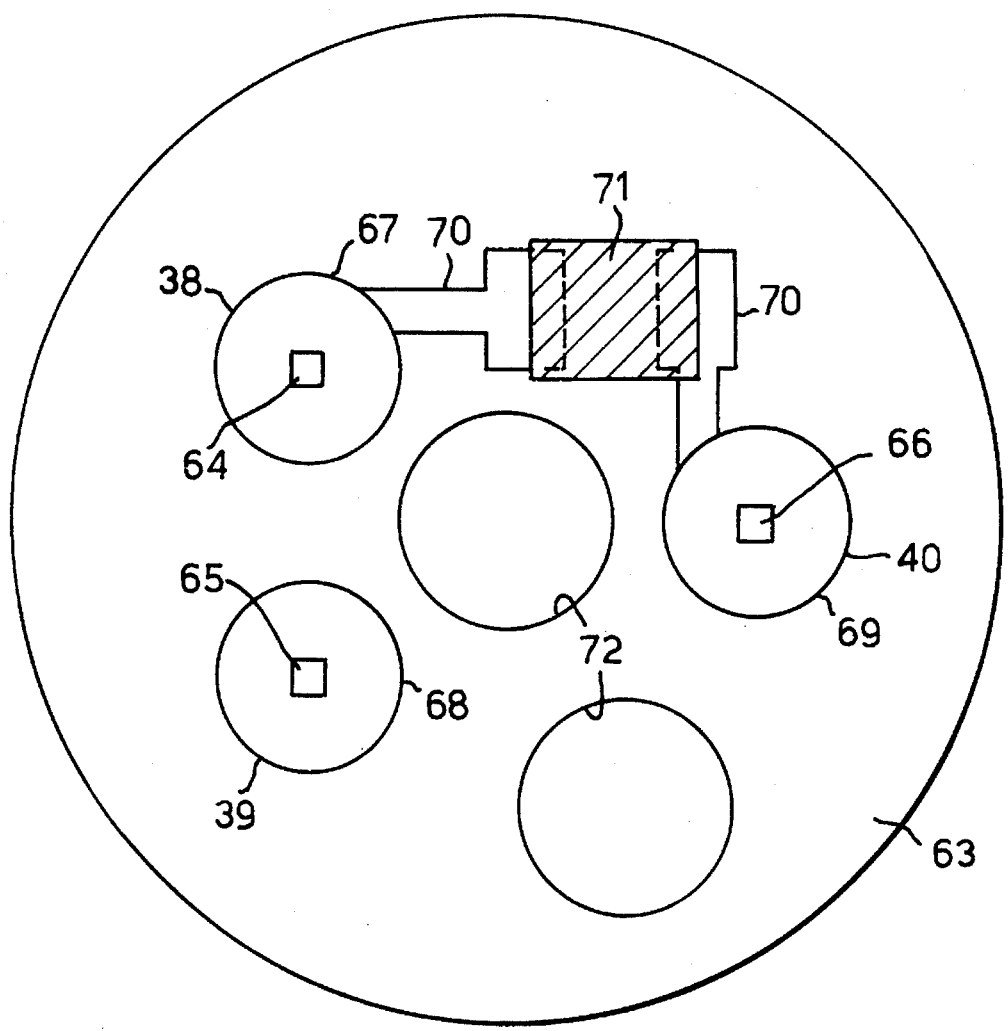

The rear closing plate 63 is mounted to the housing 24 on the other side of the potting compound 30. The underside of the rear closing plate 63 is shown in more detail in FIG. 9. The plate 63 is in the form of a printed circuit board having three apertures 64–66 through which the connectors 38–40 respectively extend. Surrounding these apertures 64–66 are respective metallic conducting regions 67–69 to which the respective connectors 38–40 are soldered. In addition, the metallic conducting regions 66,67 are coupled via tracks 70 to a trimming resistor 71. The rear closing plate 63 also has two apertures 72 through which potting compound can be supplied.

An opening 32 defined by a flange 33 of the housing 24 allows a gas being monitored into the device whilst still affording adequate protection to the sinter layer 31.

Each element 25,26 may be manufactured on a conventional base so that the construction problems of keeping the substrate free of ceramic and catalyst do not have to be taken into account. The element is then surface mounted to the substrate 23 as described above with an adequate clearance around the bead.

Alternatively, the opening 27 in the substrate 23 is arranged to give sufficient clearance to build up a bead over a coil in situ.

Figure 6:
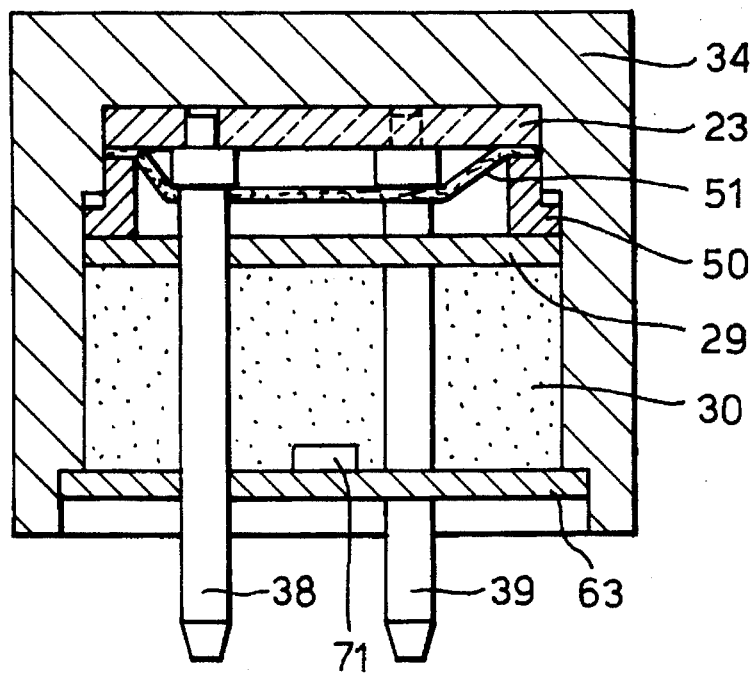
FIG. 6 is a gas sensor according to the present invention with an alternative housing arrangement.

An alternative arrangement is shown in FIG. 6. The substrate 23 is mounted in a housing 34 with the separating member 29 and the glass wool layer 51 above the elements 25,26 to separate them from the potting compound 30 which is covered by a rear closing plate 63. However, in this case, there is no separate sinter layer. Instead the housing 34 is formed of sinter throughout. This allows the overall thickness to be further reduced.

Figure 7:
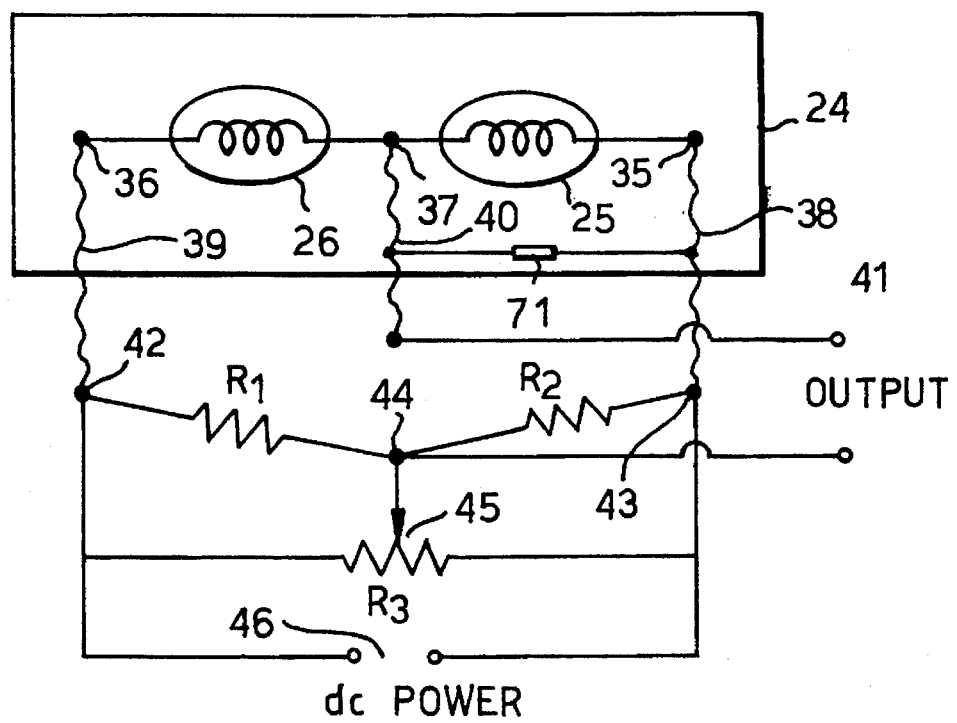
FIG. 7 is a circuit diagram of the circuit attached to the device.

FIG. 7 is a circuit diagram illustrating the connection of either of the devices shown in FIGS. 4 to 6 into a Wheatstone bridge. As can be seen in FIG. 7, the connectors 38–40 extending from the tracks at 35–37 extend out of the container 24. The connector 40 forms one output point 41 directly while the connectors 39,38 are coupled to respective resistors $R_1, R_2$ at 42,43 respectively. The resistors $R_1, R_2$ are connected at 44 to a zero set variable resistor 45 which can be adjusted between 0 and 1 kohm. The point 44 constitutes the other output pole. The trimming resistor 71 is shown connected between the connectors 38,40 and is provided to compensate for differences in performance of the elements 25,26 with temperature. DC power is supplied from a source 46 to the two points 42,43. The resistors $R_1, R_2$ would each typically be fixed at 27 ohm although in some cases these could be varied. Operation of the circuit is the same as in a conventional device.

The dimensions of a device according to the invention depend upon national regulations. For commercial reasons, it is desirable that the device should not exceed a height of 16 mm overall. However, this could not readily be achieved with a conventional sensor. European regulations require at least 3 mm of potting compound, at least 2 mm and preferably 3 mm of sinter and means for protecting the sinter from impacts. This impact protection is generally afforded by the flange 33 of the housing 24 having a thickness of about 2 mm above the sinter 31. Typically, in the present invention the separating member 29 will be of the order of 1 mm thick. The ceramic substrate 23 generally has an effective thickness of the order of 1.5 mm, while the rear closing plate 63 with resistor 71 will have a thickness of about 1.5 mm giving an overall thickness of about 12 mm. This can be accommodated in a housing 24 with a height of 16 mm. By comparison a conventional sensor incorporating the device of FIG. 1 will have a height of approximately 20 mm since the pcb mounted device is unlikely to be less than 11 mm in height itself. The separating member is not required in the conventional sensor.

Although this invention has been described in terms of catalytic oxidation devices, it will be clear that other forms of gas sensor will benefit from the reduction in height offered by the invention. This would apply in particular to gas sensors often described as semiconductor gas sensors and thermal conductivity gas sensors that are heated in a similar manner to the catalytic devices described in this patent.

I claim:

1. A device for sensing a gas, the device comprising a track carrying substrate which defines at least one aperture; at least one gas sensitive catalytic bead element wherein said element is coupled to conductors, wherein said conductors are coupled to tracks of said track carrying substrate and wherein said catalytic bead element is mounted in or adjacent to said aperture; and an inert material positioned adjacent said catalytic bead element and in said aperture to substantially prevent convection currents and improve the shock resistance of the device.

2. A device according to claim 1 further comprising a sinter layer mounted on one side of said substrate; a layer of potting compound provided on the other side of said substrate; means for protecting said sinter layer; and a separating member to isolate said at least one gas sensitive element from said potting compound.

3. A device according to claim 2 wherein said sinter layer is substantially 3 mm thick, said means for protecting said sinter layer is substantially 2 mm thick, and said layer of potting compound is not less than 3 mm thick.

4. A device according to claim 2, wherein said separating member is plastic.

5. A device according to claim 2, wherein said separating member is ceramic.

6. A device according to claim 2, wherein said separating member is a printed circuit board.

7. A device according to claim 1, further comprising a housing in which said track carrying substrate is mounted.

8. A device according to claim 7, wherein said housing is made of stainless steel.

9. A device according to claim 7, further comprising a sinter layer mounted on one side of said substrate; a layer of potting compound provided on the other side of said substrate; means for protecting said sinter layer; and a separating member to isolate said at least one gas sensitive element from said potting compound, wherein said means for protecting said sinter layer includes a part of said housing.

10. A device according to claim 1, wherein said substrate comprises a printed circuit board.

11. A device according to claim 1, wherein said inert material is one of glass and ceramic wool.

12. A device according to claim 1, wherein said element does not protrude significantly above the surface of said substrate.

13. A device according to claim 1, comprising two gas sensitive elements wherein one element is a compensating element and the other is a detecting element.

14. A device according to claim 13, wherein said catalytic bead element is preformed before mounting to said track carrying substrate.

15. A device according to claim 1, wherein said at least one gas sensitive element is positioned wholly within a respective aperture of said substrate.

16. A device according to claim 1, wherein said substrate comprises glass.

17. A device according to claim 1, wherein said substrate comprises ceramic.

* * * * *